(12) United States Patent
Ziemek et al.

(10) Patent No.: US 8,506,567 B2
(45) Date of Patent: Aug. 13, 2013

(54) OCCIPITAL PLATE FIXATION SYSTEM

(75) Inventors: Terry Ziemek, Broomfield, CO (US);
Greg Causey, Erie, CO (US); Michael Fulton, Broomfield, CO (US)

(73) Assignee: Lanx, Inc., Broomfield, CO (US)

( * ) Notice: Subject to any disclaimer, the term of this patent is extended or adjusted under 35 U.S.C. 154(b) by 684 days.

(21) Appl. No.: 12/635,559

(22) Filed: Dec. 10, 2009

(65) Prior Publication Data

US 2010/0222779 A1    Sep. 2, 2010

Related U.S. Application Data

(60) Provisional application No. 61/206,803, filed on Feb. 4, 2009.

(51) Int. Cl.
*A61B 17/56* (2006.01)
*A61B 17/80* (2006.01)
*A61F 2/44* (2006.01)

(52) U.S. Cl.
USPC ........................ 606/71; 606/296; 623/17.11

(58) Field of Classification Search
USPC ........ 606/70, 71, 280–299; 623/17.11–17.16
See application file for complete search history.

(56) References Cited

U.S. PATENT DOCUMENTS

| | | |
|---|---|---|
| 4,836,193 A | 6/1989 | Ransford |
| 4,841,959 A | 6/1989 | Ransford |
| 5,360,429 A | 11/1994 | Jeanson et al. |
| 5,423,826 A | 6/1995 | Coates et al. |
| 5,507,745 A | 4/1996 | Logroscino et al. |
| 5,542,946 A | 8/1996 | Logroscino et al. |
| 5,545,164 A | 8/1996 | Howland |
| 5,558,674 A | 9/1996 | Heggeness et al. |
| 5,651,789 A | 7/1997 | Cotrel |
| 5,707,372 A | 1/1998 | Errico et al. |
| 5,928,233 A | 7/1999 | Apfelbaum et al. |
| 6,017,343 A | 1/2000 | Rogozinski |
| 6,106,526 A | 8/2000 | Harms et al. |
| 6,146,382 A | 11/2000 | Hurlbert |

(Continued)

FOREIGN PATENT DOCUMENTS

| | | |
|---|---|---|
| EP | 0737449 | 10/1996 |
| EP | 0744923 A1 | 12/1996 |

(Continued)

OTHER PUBLICATIONS

International Search Report and Written Opinion issued Sep. 6, 2010 for International Application No. PCT/US2010/022130.

*Primary Examiner* — Matthew Lawson
(74) *Attorney, Agent, or Firm* — Perkins Coie LLP

(57) ABSTRACT

There are provided orthopedic fixation systems for attachment of a rod to bone. In an embodiment, plate having top and bottom surfaces includes at least one pocket formed through the surfaces to engage an anchor to bone. At least one arm extends from the longitudinal section of the plate. A housing portion has a base configured for slideable engagement with a course defined in the arm to allow selective positioning of the housing portion. The housing defines a passageway for slideable engagement with a rod to allow selective positioning of the rod. A ring has an inner surface for engagement with the housing portion and a lower surface for engagement with the plate. Locking apparatus is configured for engagement with the arm, housing, and rod to allow selective fixation of (1) the housing along the arm and (2) the rod and the housing with respect to one another.

30 Claims, 16 Drawing Sheets

(56) References Cited

U.S. PATENT DOCUMENTS

| | | |
|---|---|---|
| 6,187,005 B1 | 2/2001 | Brace et al. |
| 6,238,396 B1 | 5/2001 | Lombardo |
| 6,368,351 B1 | 4/2002 | Glenn et al. |
| 6,375,656 B1 | 4/2002 | Faure |
| 6,379,358 B1 | 4/2002 | Kuo |
| 6,485,491 B1 | 11/2002 | Farris et al. |
| 6,524,315 B1 | 2/2003 | Selvitelli et al. |
| 6,547,790 B2 | 4/2003 | Harkey, III et al. |
| 6,902,565 B2 | 6/2005 | Berger et al. |
| 6,949,123 B2 | 9/2005 | Reiley |
| 7,303,563 B2 | 12/2007 | Poyner et al. |
| 2002/0049446 A1 | 4/2002 | Harkey, III et al. |
| 2002/0091389 A1 | 7/2002 | Faure |
| 2003/0004512 A1 | 1/2003 | Farris et al. |
| 2003/0163132 A1 | 8/2003 | Chin |
| 2004/0153070 A1 | 8/2004 | Barker et al. |
| 2005/0080417 A1 | 4/2005 | Alexis et al. |
| 2005/0124994 A1 | 6/2005 | Berger et al. |
| 2005/0154393 A1 | 7/2005 | Doherty et al. |
| 2005/0197660 A1 | 9/2005 | Haid, Jr. et al. |
| 2005/0240181 A1 | 10/2005 | Boomer et al. |
| 2005/0240185 A1* | 10/2005 | Boomer et al. ............... 606/69 |
| 2005/0288669 A1* | 12/2005 | Abdou ........................... 606/61 |
| 2006/0004363 A1 | 1/2006 | Brockmeyer et al. |
| 2006/0155283 A1 | 7/2006 | Doherty et al. |
| 2006/0217723 A1 | 9/2006 | Suh |
| 2006/0229610 A1 | 10/2006 | Piehl |
| 2006/0229611 A1 | 10/2006 | Avery et al. |
| 2007/0016189 A1 | 1/2007 | Lake et al. |
| 2007/0118121 A1 | 5/2007 | Purcell et al. |
| 2007/0123869 A1 | 5/2007 | Chin et al. |
| 2007/0123872 A1 | 5/2007 | Brockmeyer et al. |
| 2007/0233119 A1 | 10/2007 | Markworth et al. |
| 2007/0299441 A1 | 12/2007 | Hoffman et al. |
| 2008/0177313 A1* | 7/2008 | Lemoine et al. .............. 606/250 |

FOREIGN PATENT DOCUMENTS

| | | |
|---|---|---|
| EP | 0760631 A1 | 3/1997 |
| EP | 0744923 B1 | 6/1999 |
| EP | 1317215 A2 | 6/2003 |
| EP | 1372501 A2 | 1/2004 |
| EP | 1459690 A1 | 9/2004 |
| EP | 1372501 B1 | 12/2004 |
| EP | 1317215 B1 | 12/2005 |
| EP | 1459690 B1 | 6/2006 |
| WO | WO 9531147 | 11/1995 |
| WO | WO 9723170 | 7/1997 |
| WO | WO 9841160 | 9/1998 |
| WO | WO 9918877 | 4/1999 |

* cited by examiner

OCCIPITAL PLATE FIXATION SYSTEM

REFERENCE TO PENDING PRIOR PATENT APPLICATION

This application claims the benefit under 35 U.S.C. 119 (e) of U.S. Provisional Patent Application No. 61/206,803, filed Feb. 4, 2009 by Terry Ziemek for "OCCIPITAL PLATE FIXATION SYSTEM," which patent application is hereby incorporated herein by reference.

BACKGROUND

Orthopedic fixation devices may be configured to stabilize bones. An example of a fixation device is a plate attachable to a bone portion. The plate may be connected to separate bone or another portion of the same bone. This may be accomplished with or without other connecting devices.

For spinal applications, one or more rods may run longitudinally along the spine and connect to the plate. Additional devices, such as vertebral mounts, cables, wires, hooks, screws, or other connectors may be attached to a vertebra and connected to the rod as well.

One difficult portion of the spine is the location about the skull of a patient. Occipital bone plates have been developed to provide anchor locations for spinal rod fixation to the skull of a patient.

Conventionally, plates may be chosen from a set of plates provided in multiple sizes or geometries. This requires higher costs and the need for a relatively large inventory of plates. A surgeon selects the plate from the inventory that best fits the patient anatomy. Sizing and selecting the plate generally increases the length of a surgical procedure. For example, a surgeon may need to position multiple plates at the patient's occipital region until the best fitting plate is selected with a satisfactory size and orientation for fixation of the rods.

Despite a longstanding interesting in spinal treatment, there is a need in the industry for improved fixation systems that reduce inventory and surgery duration while still providing a secure and reliable connection between the rod and the occipital or other bone structure.

BRIEF DESCRIPTION OF THE DRAWINGS

Illustrative embodiments of the invention are illustrated in the drawings, in which.

DETAILED DESCRIPTION

Figure 1:
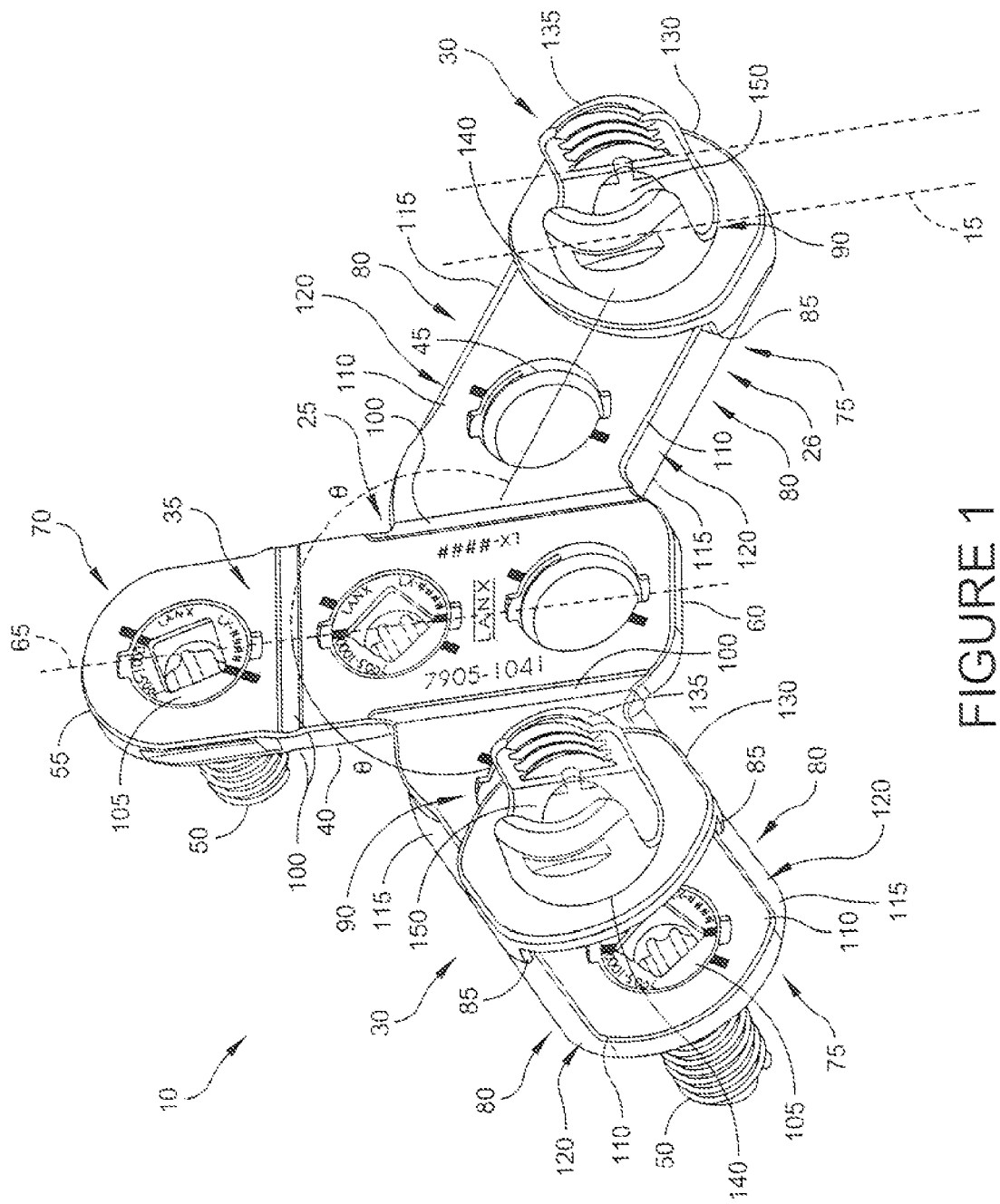
FIG. 1 illustrates a perspective view of an exemplary embodiment of an occipital plate having adjustable rod connectors mounted on opposing lateral arms.

Reference will now be made to the figures to describe embodiments of the present application. The embodiments generally described include a plate, one or more bone fasteners, and one or more spinal fixation rods. Throughout this specification, the embodiments will be described in the context of a plate to be attached between the occipital bone of the skull and the cervical spine. However, it is to be understood that the embodiments may be configured for use in other regions of the spine including other portions of the cervical spine, the thoracic spine, and/or lumbar spine. The plate may be provided in a variety of sizes, but is designed to provide multiple orientations and/or configurations to reduce the number of sizes necessary to accommodate various patient anatomies. The plate may include openings, scoring, surface fractures, or the like to facilitate tissue in-growth from the spine. Moreover, the plate may be coated or used with material to facilitate tissue in-growth, such as, for example, bone morphogenic proteins or the like.

With specific reference to FIGS. 1-6, an orthopedic fixation system 10 for attachment of a rod 15 (shown in phantom in FIGS. 1, 2 and 5) to a bone portion 20 (FIG. 5) is shown. In an embodiment, fixation system 10 includes a plate 25 and at least one housing portion 30. As will be explained further below, plate 25 may be designed with a plurality of arms 75. In one embodiment, there is provided a plurality of housing portions 30 corresponding to the plurality of arms 75. As shown in the exemplary embodiment, plate 25 has two arms 75 and a corresponding two housing portions 30.

Plate 25 may have a top surface 35 and a bottom surface 40 in opposition to one another. Top surface 35 and bottom surface 40 are provided for relative orientation and description. Plate 25 generally has sidewalls 26 extending between top surface 35 and bottom surface 40. Top surface 35 is generally configured to receive housing portion 30. Housing portion 30 extends away from top surface 35 and bone portion 20 and provides a saddle to which rod 15 may be coupled, as will be explained further below. Bottom surface 40 is generally configured for placement against a bone portion 20. At least one pocket 45 may be formed through top surface 35 and bottom surface 40. Pocket 45 may be an appropriate shape to accommodate a corresponding anchor 50. Pocket 45 is, in this example, a bore shaped to accommodate an anchor 50 comprising a bone screw. Generally pocket 45 will have a first diameter proximate top surface 35 that allows passage of anchor 50, including both a threaded shaft and head in this example, and a second diameter proximate bottom surface 40 that allows passage of the shaft of anchor 50 but not the head of anchor 50. Thus, plate 25 may be secured to bone portion 20 with one or more anchors 50. Although described with relation to threaded bone screws, pockets 45 and anchors 50 may accommodate other types of bone fasteners such as, for example, pins, rivets, nails, spikes, or the like. Moreover, other fasteners may be used such as, for example, staples, hooks, sutures, wires, straps, clamps, teeth, adhesives, and/or other suitable fasteners.

Figure 2:
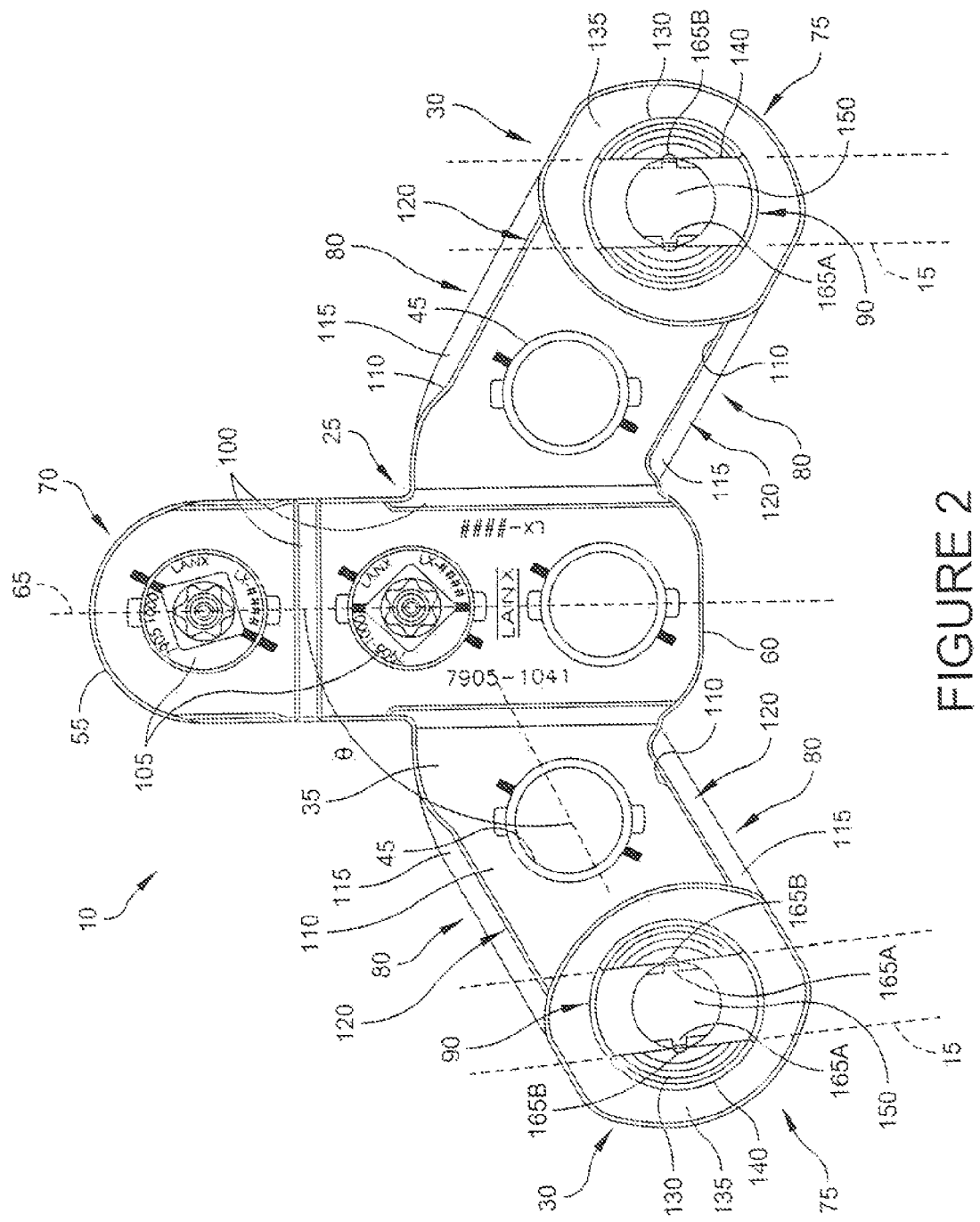
FIG. 2 illustrates a top plan view of the occipital plate of FIG. 1.
Figure 3:
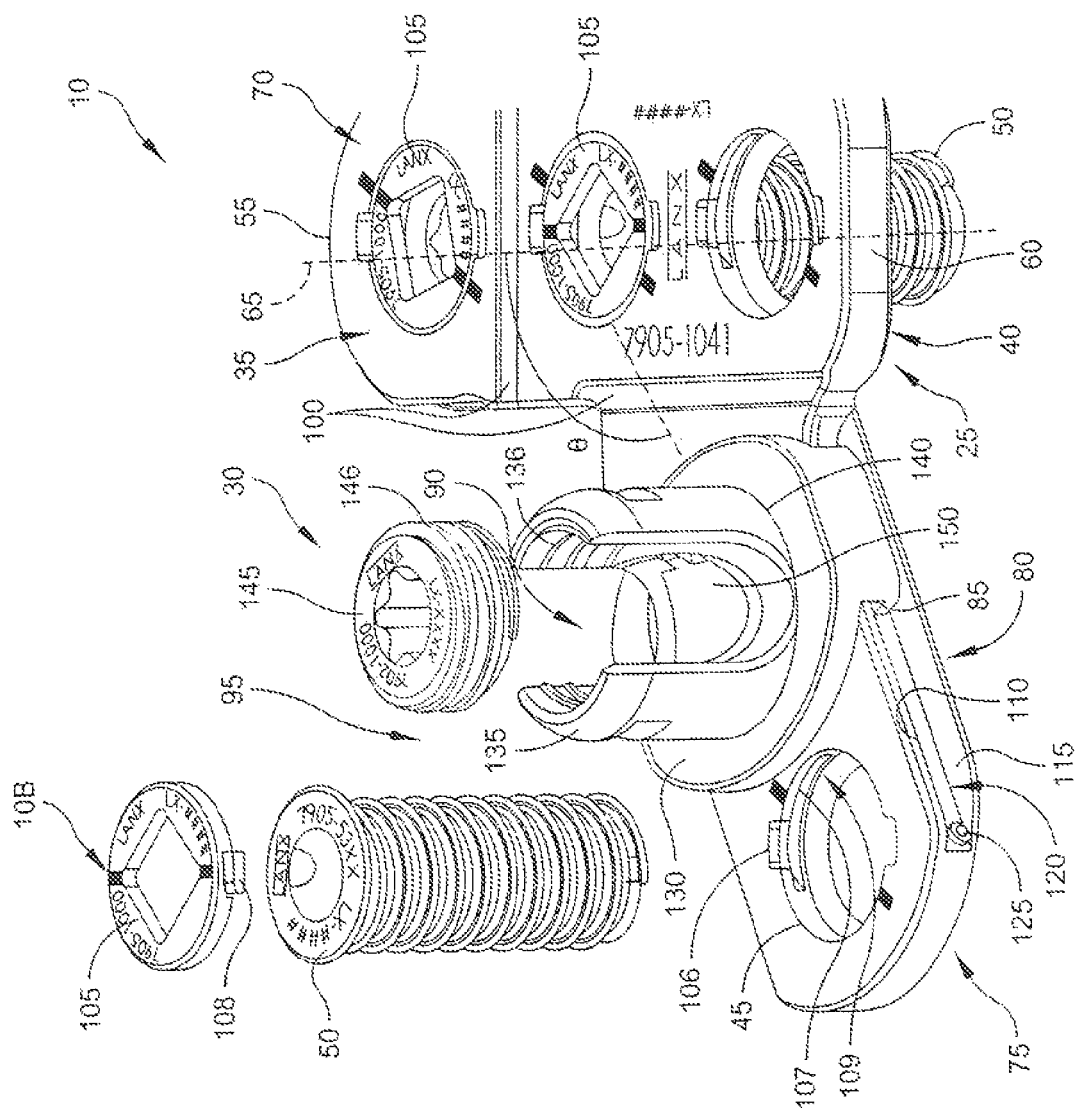
FIG. 3 illustrates a partially exploded schematic view of the occipital plate with a set screw, a saddle, the rod seat, and a carrier forming a housing portion for adjustably fixing a rod to the plate, and an anchor screw with a locking cap positioned above a pocket extending through an arm of the plate.

Looking at FIGS. 1-3, plate 25 is illustrated with a first end 55 and a second end 60 in opposition to one another. A longitudinal axis 65 extends between first end 55 and second end 60 defines a longitudinal section 70 of plate 25. Arms 75 extend at an angle θ from longitudinal section 70 of plate 25. A set of rails 80 may be defined in opposition to one another along each of arms 75. While shown as an obtuse angle, angle θ may be either an acute or obtuse angle depending on the patient anatomy and configuration. Angle 6 also may be a right angle, in which longitudinal section 70 and arms 75 form a generally "T-shaped" configuration.

As explained earlier, each housing portion 30 resides on an arm 75. Arm 75 is provided with rails 80. Rails 80 are formed by channels or recesses in the sidewalls 26 of plate 25.

Housing portion 30 has a set of flanges 85 configured for slideable engagement with rail 80 in the corresponding arm 75. Flange 85 in this embodiment is generally formed in a hook shape such that flange 85 extends along sidewall 26 and into the channel or recess formed by rail 80. This allows selective positioning of housing portion 30 along a length of one of the arms 75. The selective positioning in turn allows rods 15 to be positioned closer or further apart without having to provide different plates having housing portions 30 positioned closer or further apart.

Housing portion 30 provides a passageway 90 or channel configured for slideable engagement with rod 15. This allows selective positioning of rod 15 and housing portion 30 with respect to one another. Thus, arm 75, housing portion 30, and rod 15 may be selectively placed and oriented to allow selective fixation of (1) housing portion 30 along one of the arms 75 and (2) rod 15 and housing portion 30 with respect to one another.

In one embodiment, at least one pocket 45 is provided in longitudinal section 70. In the example provided, a plurality of pockets 45 are provided in longitudinal section 70. A greater number of pockets 45 allows additional anchors 50 to be used which may provide increased stability of plate 25 and, in turn, rods 15 in connection with bone portion 20.

Optionally, one or more plate bending zones 100 may be provided. The plate bending zones 100 are shown as a portions of plate 25 that have a decreased thickness, i.e., are thinner, to allow the plate to have some elastic or inelastic deformation without breaking. Plate bending zones 100 may be provided on any portion of plate 25 where it may be necessary or desirable to bend the plate due to patient anatomy. For example, plate bending zones 100 are provided between longitudinal section 70 and each arm 75. Also, a plate bending zone 100 also may be provided in longitudinal section 70, which may accommodate the spine to skull connection. Plate bending zones 100 permit plate 25 to be more securely attached with a low profile to bone portion 20, such as a curved occipital region.

Figure 5:
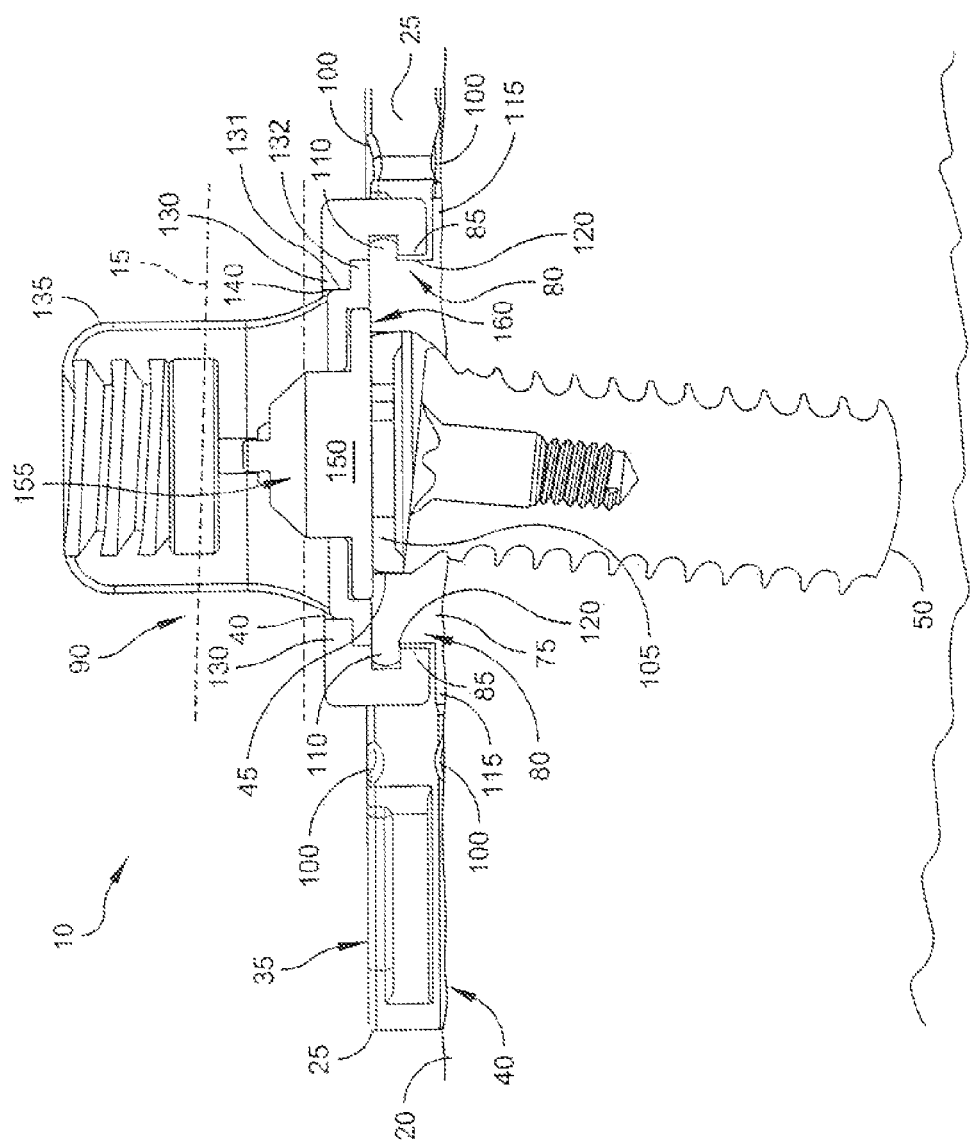
FIG. 5 is a cross-sectional view of the housing portion in attachment with the plate in a position with the anchor screw below the rod seat.
Figure 6:
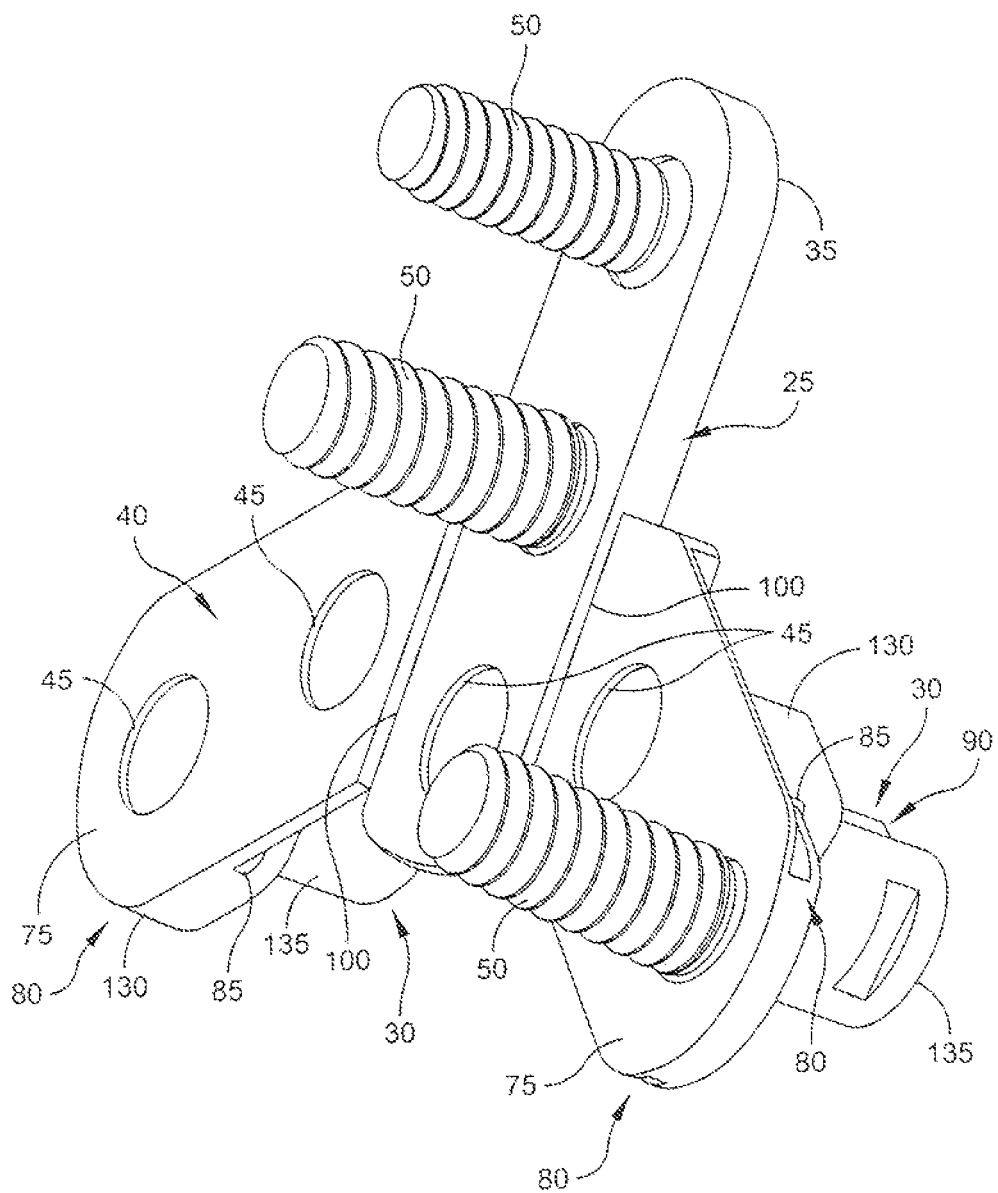
FIG. 6 illustrates a perspective view of the bone engaging side of the occipital plate.

As best illustrated in FIGS. 1 and 5, housing portion 30 may be configured to pass over anchors 50 disposed in the pocket 45 formed in one of the arms 75. In other words, anchors 50 are recessed into top surface 35 of plate 25. In addition, housing portion 30 may be configured to lock in a position over at least one pocket 45 formed in one of the arms 75. As discussed above, this selective positioning allows rods 15 to be positioned closer or further apart across a wide portion of arms 75 without having to select the plate from ones having various sized openings. Moreover, housing portion 30 may act to inhibit anchors 50 from reverse threading.

At least one pocket 45 may be configured to receive a screw locking cap 105 (FIGS. 1, 3, and 5). Screw back out or reverse threading may be prevented by using locking cap 105. Alternatively, screw back out or reverse threading may be accomplished by other conventional means, such as, for example, a bushing, a snap ring, a taper lock, adhesives, resilient rings, washers, or the like that are generally known in the art. Referring to FIG. 3, screw locking cap 105 shaped as a ring with a passage to allow a driver to engage anchor 50. Screw locking cap 105 has at least one, but preferably a plurality of protrusions 108. Pocket 45 has at least one access port 107 formed in top surface 35 that provides access to channel 106 that is provided as an annular channel about pocket 45. The number of access ports 107 conforms to or is more than the number of protrusions 108. Channel 106 has one or more lips 109 or narrowings in channel 106. Screw locking cap 105 is secured to plate 25 by aligning the protrusions 108 with access ports 107 and turning screw locking cap 105 such that protrusions 108 move along channel 106. Sufficient torque would need to be applied to move protrusions 108 past lip 109 to secure screw locking cap 105 in pocket 45, which prevents anchor 50 from reverse threading or backing out. For example, lip 109 may be an elastic composite material that provides rotational resistance.

Housing portion 30 may be configured to pass over and/or be secured above screw locking cap 105, which may be disposed over anchor 50 in pocket 45.

As discussed above, this selective positioning allows rods 15 to be positioned closer or further apart across a wider portion of arms 75 without having to select the plate from ones having various sized openings.

Referring to FIG. 5, and in one embodiment, a pocket 45 may be formed having a spherical inner surface to match a spherical external surface of a head of anchor 50. Forming pocket 45 with the spherical inner surface to match the spherical external surface of the head of anchor 50 may allow anchor 50 to be configured in a number of angular orientations with respect to plate 25. The optional positioning allows rods 15 to be positioned in various orientations without having to select the plate from ones having various types of fixation hardware. Providing a bore to allow multiple angular orientation of anchor 50 is generally known in the art and will not be further explained herein.

As illustrated in FIGS. 1-6, the pair of arms 75 may each form an angle θ of greater than 90° with longitudinal section 70 of plate 25. In other embodiments, arms 75 may be orthogonal to longitudinal section 70 or may include other shapes, such as a delta. In another embodiment, rails 80 may be provided in plate 25 without distinctly formed "arms".

Referring to FIGS. 1-4, the rails 80 formed in sidewalls 26 may be formed with a top shelf 110 and a bottom shelf 115. A channel 120 may be provided between top shelf 110 and bottom shelf 115 for receipt of flanges 85 of housing portion 30. In an embodiment, rails 80 may run along substantially all of the length of arm 75. In another embodiment, rails 80 may run along only a portion of the length of arm 75. In addition, rails 80 may be configured to extend into longitudinal section 70 or may be configured to remain within a central portion of the length of arm 75.

Figure 4:
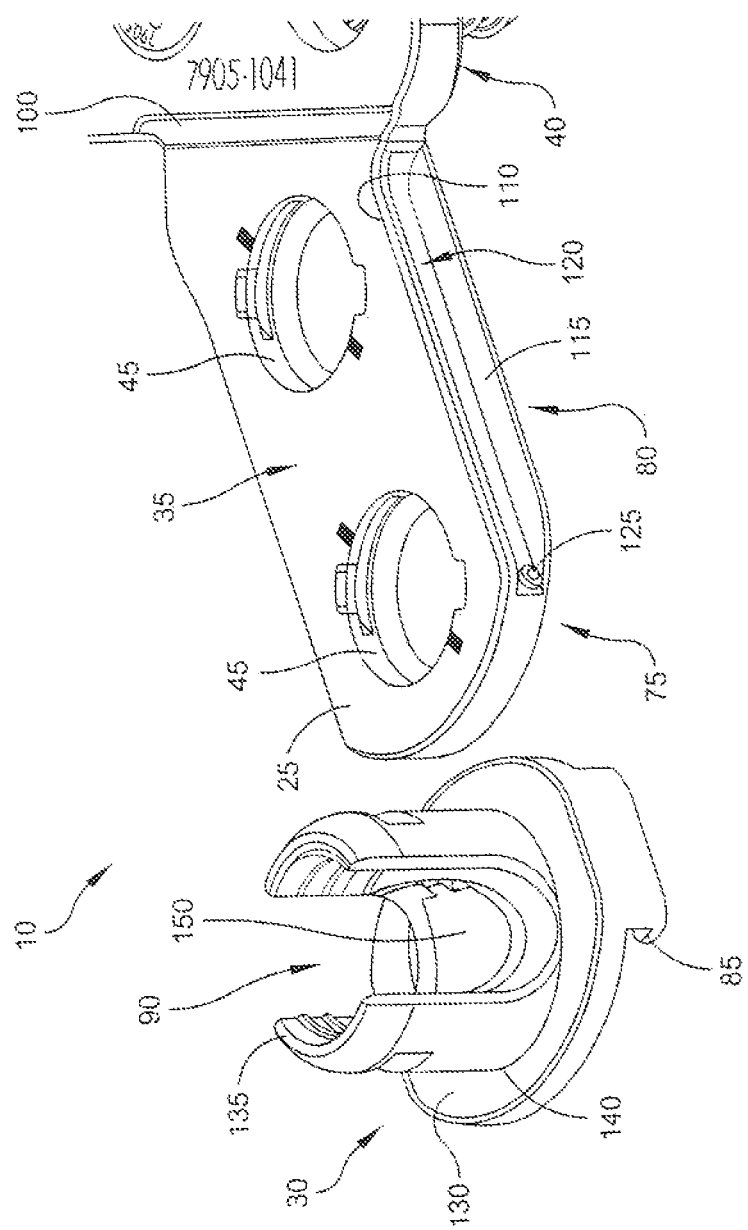
FIG. 4 illustrates the housing portion disposed away from the arm portion of the plate.

Looking at FIGS. 3 and 4, a limiter 125 may be provided in channel 120 to prevent the one of the flanges 85 from leaving the set of rails 80. In one embodiment, limiter 125 may be selectively removable from channel 120. Limited 125 may be selectively removable from channel 120 by a threaded connection, a snap lock connection, a friction fit connection, sutured, stapled, and or clamped into channel 120. In another embodiment, limiter may be fixedly positioned to block channel 120. Limiter 125 may be replaced by extending sidewall 26 such that channel 120 is terminated by a part of plate 25.

For a removable configuration, housing portion 30 may be attached to plate 25 during surgery. In addition, housing portion 30 may be attached to plate 25 after it is attached to bone portion 20 in some instances. For a fixedly positioned configuration, housing portion 30 may be provided in attachment to plate 25 prior to surgery.

As best shown in FIG. 5, the set of flanges 85 may be disposed toward one another. In this configuration, flanges 85 wrap around top surface 35 of plate 25 and secure housing portion to arm 75. This configuration allows travel of housing portion 30 within channel 120 of the rails 80 while remaining along top surface 35 of the plate 25.

Housing portion 30 may include a carrier 130 and a saddle 135. Carrier 130 may include flanges 85 and may form an opening 140 sized to rotatably retain saddle 135. In one embodiment, carrier 130 may have a shoulder 131 extending into opening 140. Saddle 135 may have rim 132 extending under shoulder 131 such that carrier 130 and saddle 135 are rotatably coupled, although any suitable connection is possible. Having saddle 135 rotatably coupled to carrier 130 allows for selective orientation of rod 15 and housing portion 30. Housing portion 30 may include a set screw 145 sized for engagement with saddle 135 such as by a threaded engagement between internal threads 136 in saddle 135 and corresponding external threads 146 on set screw 145 as shown although any compression fitting as is generally known in the art is useable. Set screw 145 and saddle 135 may be configured to selectively retain rod 15 when set screw 145 is tightened a predetermined amount into saddle 135. The selective rotation of saddle 135 with respect to carrier 130 allows rods 15 to be positioned in various orientations without having to select from various sized attachment apparatus to provide alternative orientations.

Referring to FIGS. 1-5, there is shown a rod seat 150 disposed within saddle 135. Rod seat 150 may include an upper end 155 (FIG. 5) and a lower end 160 (FIG. 5) in opposition to one another. Upper end 155 may be, configured to engage rod 15 within the saddle 135. Lower end 160 may be configured to engage top surface 35 of plate 25.

As best illustrated in FIG. 5, lower end 160 of rod seat 150 may extend a longer distance than a width of pocket 45. This allows selective fixation of housing portion 30 over pocket 45 along one of the arms 75. It is important to appreciate the geometry of rod seat 150 which allows housing portion 30 to be positioned along a length of arm 75 with various features below. Rod seat 150 provides the conduit for a pressure fit engagement between set screw 145, rod 15, and plate 25. This configuration also allows rotation and translation of housing portion 30 prior to tightening of set screw 145, without requiring additional adjustments prior to fixation of housing portion 30 after positioning apart from the tightening of set screw 145.

In one embodiment, rod seat 150, saddle 135, and set screw 145 may be sized to lock rotation of rod 15 and lock translation of saddle 135 with respect to carrier 130 when set screw 145 is tightened a predetermined amount onto rod 15. In one embodiment, rod seat 150, saddle 135, and set screw 145 may be sized to lock rotation of rod 15 chosen from a range of diameters. The range of diameters may include rods of about 3.5 mm to about 4.0 mm. As set screw 145 is tightened, rod 15 may become locked into a fixed position by pressing an engagement surface of set screw 145 into rod 15 and lower end 160 of rod seat 150 against top surface 35 of plate 25, the saddle 135 is drawn up and rim 132 binds with shoulder 131 of carrier 130 causing flange 85 of housing portion 30 to secure with channel 120 of plate 25.

Rod seat 150 may be configured with a keyed profile 165A. Housing portion 30 may form a corresponding profile 165B to keyed profile 165A of rod seat 150. These keyed profiles position rod seat 150 for receipt of rod 15 within channel 90. In other words, rod seat 150 is aligned to receive rod 15 within passageway 90.

In an embodiment, carrier 130 and saddle 135 may be formed to allow a 360° rotation of saddle 135 with respect to carrier 130 although rotation of about 180° would effectively provide 360° of rotation. As discussed above, the selective rotation of saddle 135 prior to fixation with set screw 145 allows rod 15 to be positioned in various orientations without having to select from various sized attachment apparatus to provide alternative orientations.

As mentioned above, top shelf 110 and bottom shelf 115 are formed to provide channel 120 to allow adjustment of housing portion 30. Bottom shelf 115 may be formed to keep debris out of channel 120 and maintain channel 120 for adjustment of housing portion 30. For example, bottom shelf 115 may extend a greater distance than top shelf 110. This greater extension of 115 provides a larger area of bottom surface 40 of plate 25 on bone portion 20 and provides an area to protect channel 120 containing flange 85.

In an embodiment (not shown), an add-on expansion may be provided for both or of one of the pair of arms 75. A connector of the expansion add-on may be configured to attach to the set of rails 80 of one of the pair of arms 75.

In an embodiment, housing portion 30 and plate 25 may be configured to allow attachment of housing portion 30 to plate 25 after plate 25 has been attached to bone portion 20. With this configuration, a surgeon may install plate 20 to bone portion 20 and then select which housing portions will be attached to plate 20.

It should be appreciated that bone portion 20 may be a single bone. Alternatively, bone portion 20 may include several different anchor points. In one embodiment, bone portion 20 is an occipital bone.

Figure 7:
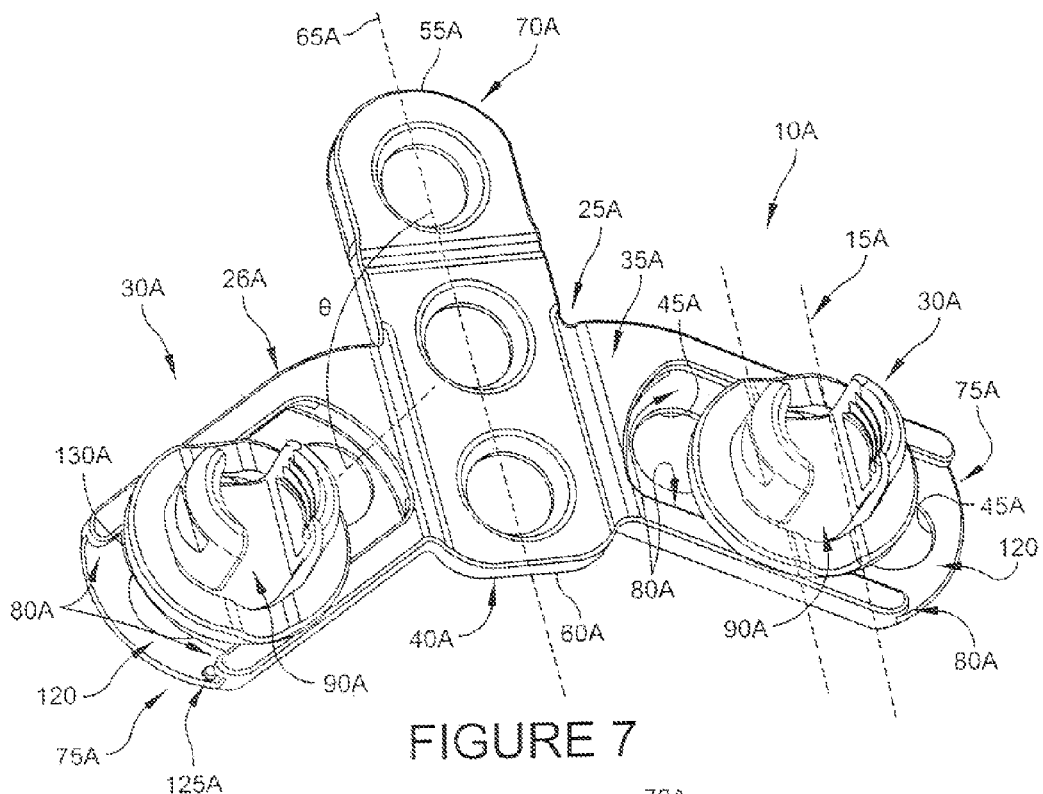
FIG. 7 illustrates a perspective view of another exemplary embodiment of an occipital plate having adjustable rod connectors mounted on opposing lateral arms.
Figure 8:
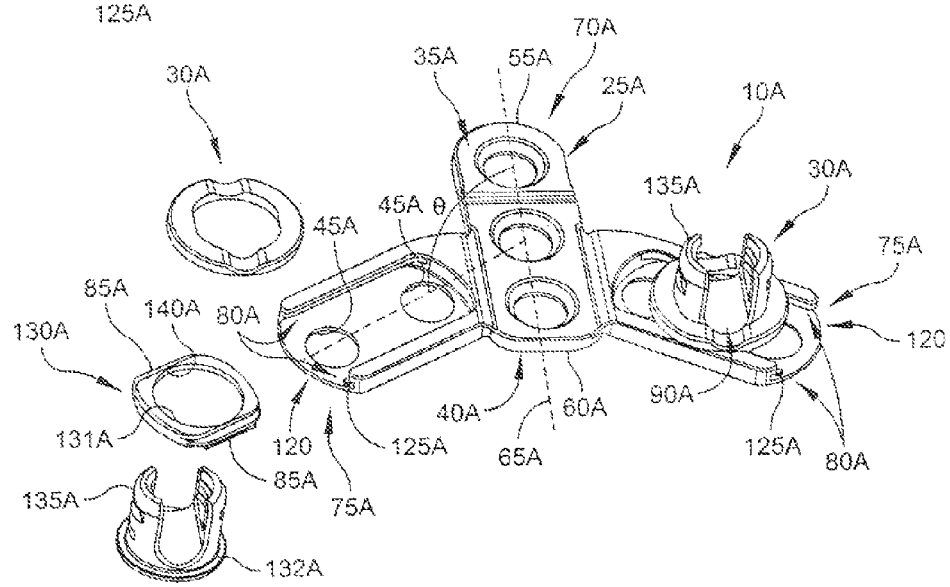
FIG. 8 illustrates a partially exploded schematic view of the occipital plate with a saddle, a carrier, and a retaining ring forming a housing portion for adjustably fixing a rod to the plate, and an anchor screw with a locking cap positioned above a pocket extending through an arm of the plate.

With specific reference to FIGS. 7 and 8, an orthopedic fixation system 10A for attachment of a rod 15A (shown in phantom in FIG. 7) to a bone portion is shown. In an embodiment, fixation system 10A includes a plate 25A and at least one housing portion 30A. As will be explained further below, plate 25A may be designed with a plurality of arms 75A. In one embodiment, there is provided a plurality of housing portions 30A corresponding to the plurality of arms 75A. As shown in the exemplary embodiment, plate 25A has two arms 75A and a corresponding two housing portions 30A.

Plate 25A may have a top surface 35A and a bottom surface 40A in opposition to one another. Top surface 35A and bottom surface 40A are provided for relative orientation and description. Plate 25A generally has sidewalls 26A extending between top surface 35A and bottom surface 40A. Top surface 35A is generally configured to receive housing portion 30A. Housing portion 30A extends away from top surface 35A and bone portion and provides a saddle to which rod 15A may be coupled, as will be explained further below. Bottom surface 40A is generally configured for placement against a bone portion. At least one pocket 45A may be formed through top surface 35A and bottom surface 40A. Pocket 45A may be an appropriate shape to accommodate a corresponding anchor (e.g., anchor 50 illustrated in FIG. 1.) Pocket 45A is, in this example, a bore shaped to accommodate an anchor comprising a bone screw. Thus, plate 25A may be secured to a bone portion with one or more anchors. Although described with relation to threaded bone screws, pockets 45A and anchors may accommodate other types of bone fasteners such as, for example, pins, rivets, nails, spikes, or the like. Moreover, other fasteners may be used such as, for example, staples, hooks, sutures, wires, straps, clamps, teeth, adhesives, and/or other suitable fasteners.

Looking at FIGS. 7 and 8, plate 25A is illustrated with a first end 55A and a second end 60A in opposition to one another. A longitudinal axis 65A extends between first end 55A and second end 60A defines a longitudinal section 70A of plate 25A. Arms 75A extend at an angle θ from longitudinal section 70A of plate 25A. A set of rails 80A may be defined in opposition to one another within each of arms 75A. While shown as an obtuse angle, angle θ may be either an acute or obtuse angle depending on the patient anatomy and configuration. Angle θ also may be a right angle, in which longitudinal section 70A and arms 75A form a generally "T-shaped" configuration.

As explained earlier, each housing portion 30A resides on an arm 75A. Arm 75A is provided with rails 80A. Rails 80A are formed by channels or recesses inside of the sidewalls 26A of plate 25A.

Housing portion 30A has a carrier 130A with a set of flanges 85A configured for slideable engagement with rail 80A in the corresponding arm 75A. Flange 85A in this embodiment is generally formed in a hook shape such that flange 85A extends along sidewall 26A and into the channel or recess formed by rail 80A. This allows selective positioning of housing portion 30A along a length of one of the arms 75A. The selective positioning in turn allows rods 15A to be positioned closer or further apart without having to provide different plates having housing portions 30A positioned closer or further apart. Housing portion 30A is rotatable relative to carrier 130A to provide further adjustability.

Housing portion 30A provides a passageway 90A or channel configured for slideable engagement with rod 15A. This allows selective positioning of rod 15A and housing portion 30A with respect to one another. Thus, arm 75A, housing portion 30A, and rod 15A may be selectively placed and oriented to allow selective fixation of (1) housing portion 30A along one of the arms 75A and (2) rod 15A and housing portion 30A with respect to one another.

In one embodiment, at least one pocket 45A is provided in longitudinal section 70A. In the example provided, a plurality of pockets 45A are provided in longitudinal section 70A. A greater number of pockets 45A allows additional anchors to be used which may provide increased stability of plate 25A and, in turn, rods 15A in connection with bone portion.

Looking at FIGS. 7 and 8, a limiter 125A may be provided in an opening channel 120A to prevent the one of the flanges 85A from leaving the set of rails 80A. In one embodiment, limiter 125A may be selectively removable from channel 120A. Limiter 125A may be selectively removable from channel 120A by a threaded connection, a snap lock connection, a friction fit connection, sutured, stapled, and or clamped into channel 120A. In another embodiment, limiter may be fixedly positioned to block channel 120A. Limiter 125A may be replaced by extending sidewall 26A such that channel 120A is terminated by a part of plate 25A. Housing portion 30A may include a carrier 130A and a saddle 135A. Carrier 130A may include flanges 85A and may form an opening 140A sized to rotatably retain saddle 135A. In one embodiment, carrier 130A may have a shoulder 131A extending into opening 140A. Saddle 135A may have rim 132A extending under shoulder 131A such that carrier 130A and saddle 135A are rotatably coupled, although any suitable connection is possible. Having saddle 135A rotatably coupled to carrier 130A allows for selective orientation of rod 15A and housing portion 30A. Housing portion 30A may include a set screw (not shown) sized for engagement with saddle 135A such as by a threaded engagement between internal threads in saddle 135A and corresponding external threads on the set screw although any compression fitting as is generally known in the art is useable. Set screw 145A and saddle 135A may be configured to selectively retain rod 15A when set screw 145A is tightened a predetermined amount into saddle 135A. The selective rotation of saddle 135A with respect to carrier 130A allows rods 15A to be positioned in various orientations without having to select from various sized attachment apparatus to provide alternative orientations. As set screw 145A is tightened, rod 15A may become locked into a fixed position by pressing an engagement surface of set screw 145A into rod 15A, pressing rim 132A of housing 30A against top surface 35A within channel 120A, and pressing rod 15 against carrier 130A or top surface 35A of plate 25.

With specific reference to FIGS. 9-20, an orthopedic fixation system 1000 for attachment of a rod 1015 (shown in phantom in FIGS. 9, 10, and 13) to a bone portion 1020 (FIG. 11) is shown. In an embodiment, fixation system 1000 includes a plate 1025 and at least one housing portion 1030. As will be explained further below, plate 1025 may be designed with a plurality of arms 1075. In one embodiment, there is provided a plurality of housing portions 1030 corresponding to the plurality of arms 1075. As shown in the exemplary embodiment, plate 1025 has two arms 1075 and a corresponding two housing portions 1030.

Figure 11:
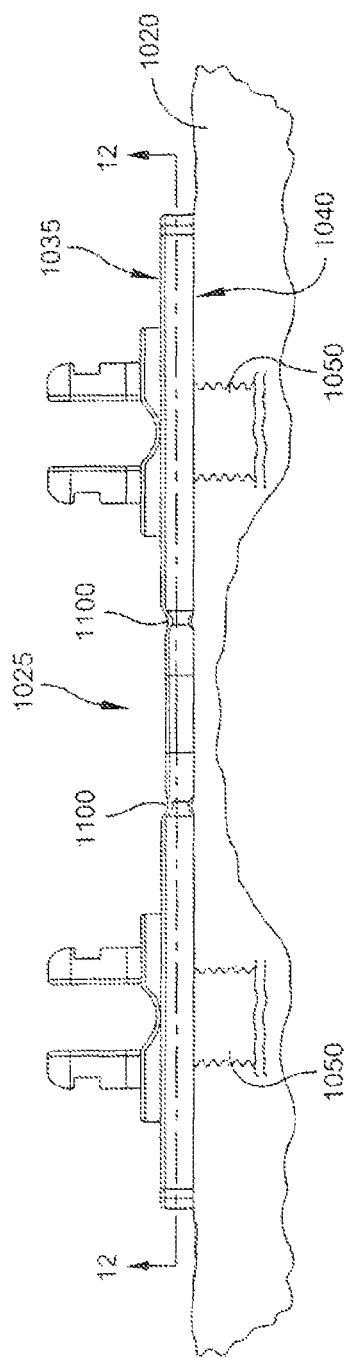
FIG. 11 illustrates an elevational view of the occipital plate of FIG. 10.

Plate 1025 may have a top or upper surface 1035 and a bottom or lower surface 1040 in opposition to one another. Top surface 1035 and bottom surface 1040 are provided for relative orientation and description. Plate 1025 generally has sidewalls 1026 extending between top surface 1035 and bottom surface 1040. Top surface 1035 is generally configured to receive housing portion 1030. Housing portion 1030 extends away from top surface 1035 and bone portion 1020 and provides a saddle to which rod 1015 may be coupled, as will be explained further below. Bottom surface 1040 is generally configured for placement against a bone portion 1020. At least one pocket 1045 may be formed through top surface 1035 and bottom surface 1040. Pocket 1045 may be an appropriate shape to accommodate a corresponding anchor 1050. (FIG. 11.) Pocket 1045 is, in this example, a bore shaped to accommodate an anchor 1050 comprising a bone screw. Generally, pocket 1045 will have a first diameter proximate top surface 1035 that allows passage of anchor 1050, including both a threaded shaft and head in this example, and a second diameter proximate bottom surface 1040 that allows passage of the shaft of anchor 1050 but not the head of anchor 1050. Thus, plate 1025 may be secured to bone portion 1020 with one or more anchors 1050. Although described with relation to threaded bone screws, pockets 1045 and anchors 1050 may accommodate other types of bone fasteners such as, for example, pins, rivets, nails, spikes, or the like. Moreover, other fasteners may be used such as, for example, staples, hooks, sutures, wires, straps, clamps, teeth, adhesives, and/or other suitable fasteners.

Figure 10:
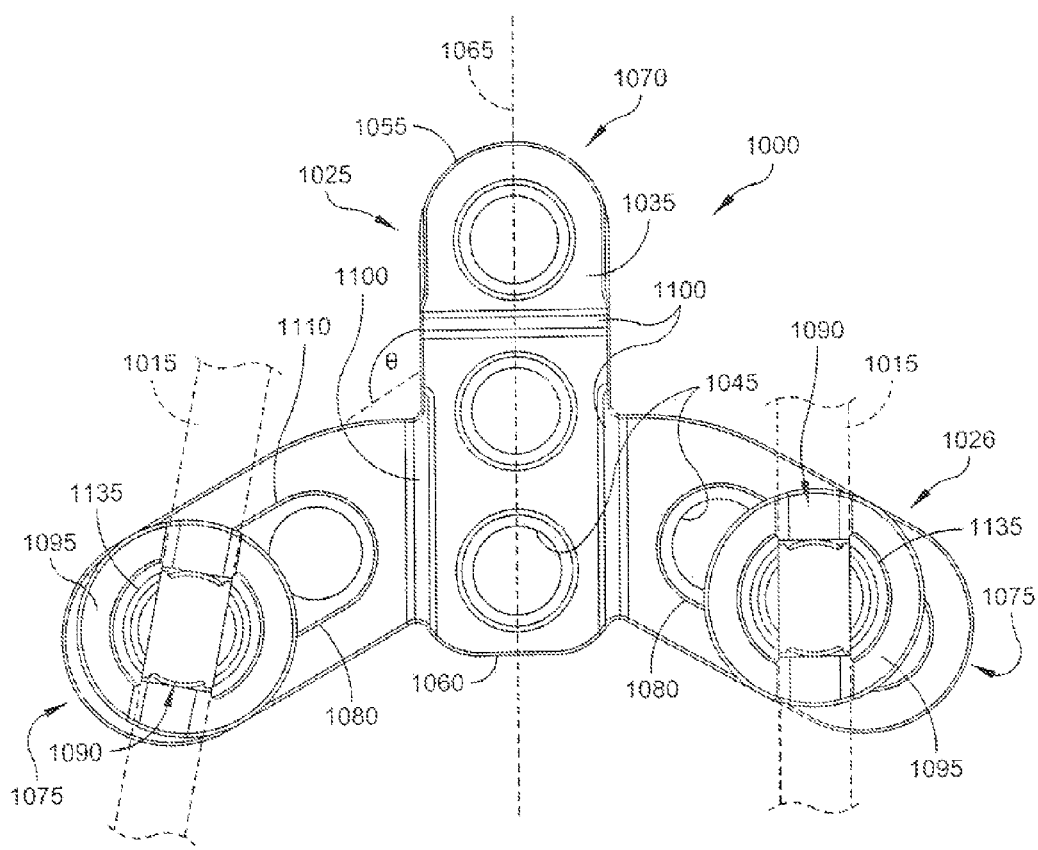
FIG. 10 illustrates a top plan view of the occipital plate of FIG. 9.

Looking at FIG. 10, plate 1025 is illustrated with a first end 1055 and a second end 1060 in opposition to one another. A longitudinal axis 1065 extends between first end 1055 and second end 1060 defines a longitudinal section 1070 of plate 1025. In some embodiments, plate 1025 has an elongate section with arms extending therefrom. Arms 1075 extend at an angle θ from longitudinal section 1070 of plate 1025. A course 1080 may be defined along each of arms 1075. While shown as an obtuse angle, angle θ may be either an acute or obtuse angle depending on the patient anatomy and configuration. Angle θ also may be a right angle, in which longitudinal section 1070 and arms 1075 form a generally "T-shaped" configuration.

As explained earlier, each housing portion 1030 resides on an arm 1075. Arm 1075 is provided with course 1080, which may be formed by a channel 1080a or recess 1080a to the interior of sidewalls 1026 of plate 1025. In some embodiments, course 1080 is more than one-half as long as a length of arm 1075.

Housing portion 1030 has a base 1085 configured for slideable engagement with channel 1080a of course 1080 in the corresponding arm 1075. Base 1085 in one embodiment is generally formed as a radially outwardly extending flange with opposing flats 1085a such that the width of the base 1085 across the flats 1085a is shorter than the length of the base perpendicular to the width. Base 1085 extends outwardly and into channel 1080a formed by course 1080. This allows selective positioning of housing portion 1030 along a length of one of the arms 1075 while preventing the housing portion 1030 from lifting away from the arm 1075. The selective positioning in turn allows rods 1015 to be positioned closer or further apart without having to provide different plates having housing portions 1030 positioned closer or further apart.

Housing portion 1030 provides a passageway 1090 or channel configured for slideable engagement with rod 1015. This allows selective positioning of rod 1015 and housing portion 1030 with respect to one another. Thus, arm 1075, housing portion 1030, and rod 1015 may be selectively placed and oriented to allow selective fixation of (1) housing portion 1030 along one of the arms 1075 and (2) rod 1015 and housing portion 1030 with respect to one another.

Figure 9:
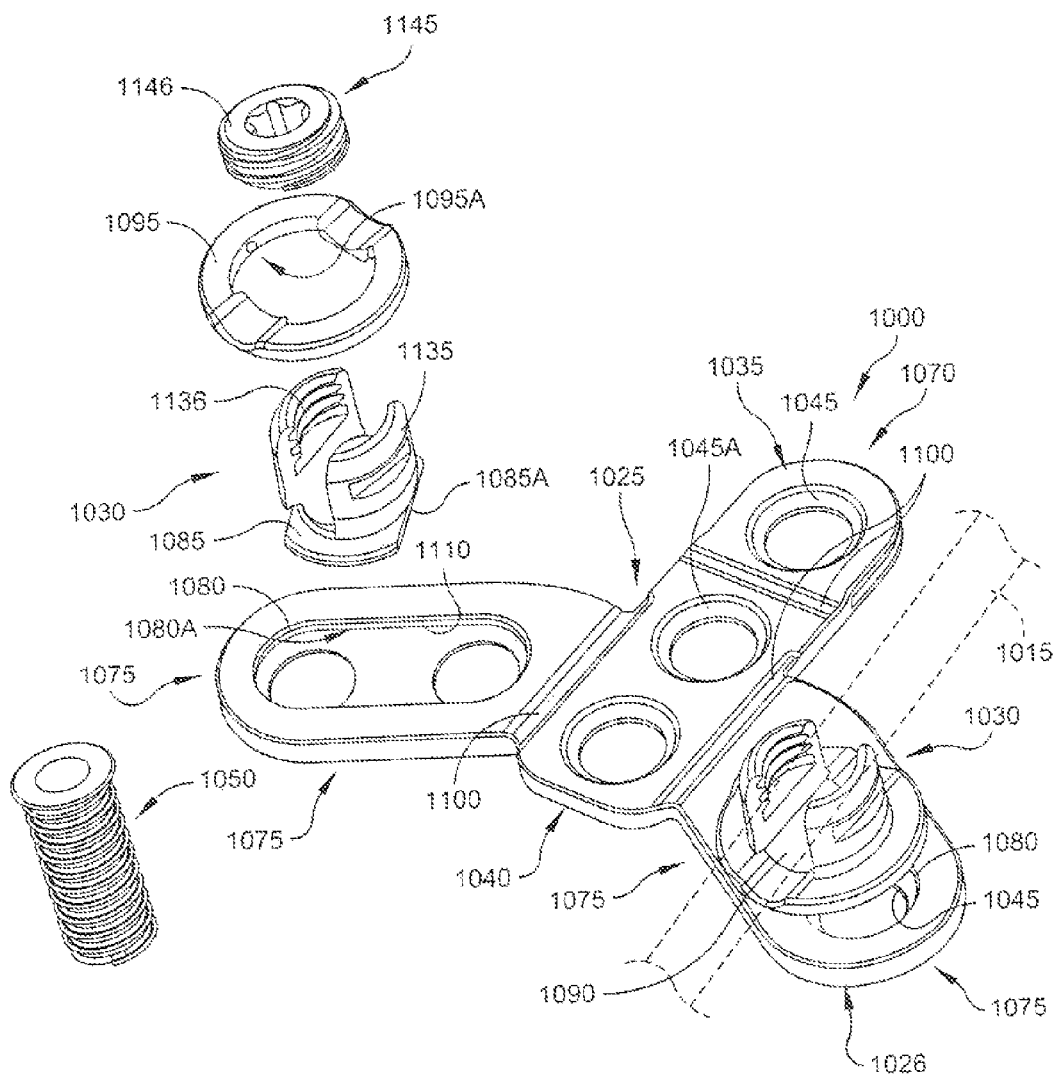
FIG. 9 illustrates a perspective view of another exemplary embodiment of an occipital plate having adjustable rod connectors mounted on opposing lateral arms.

In one embodiment, at least one pocket 1045 is provided in longitudinal section 1070. In the example provided, a plurality of pockets 1045 are provided in longitudinal section 1070. A greater number of pockets 1045 allows additional anchors 1050 to be used which may provide increased stability of plate 1025 and, in turn, rods 1015 in connection with bone portion 1020. Referring to FIG. 9, in one embodiment, a pocket 1045 may be formed having a spherical inner surface 1045A to match a spherical external surface of a head of anchor 1050. Forming pocket 1045 with the spherical inner surface to match the spherical external surface of the head of anchor 1050 may allow anchor 1050 to be configured in a number of angular orientations with respect to plate 1025. Providing a bore to allow multiple angular orientation of anchor 1050 is generally known in the art and will not be further explained herein. In some embodiments, one or more pockets 1045 are formed through arm 1075, and may be formed within course 1080.

Optionally, one or more plate bending zones 1100 may be provided. The plate bending zones 1100 are shown as a portions of plate 1025 that have a decreased thickness, i.e., are thinner, to allow the plate to have some elastic or inelastic deformation without breaking. Plate bending zones 1100 may be provided on any portion of plate 1025 where it may be necessary or desirable to bend the plate due to patient anatomy. For example, plate bending zones 1100 are provided between longitudinal section 1070 and each arm 1075. Also, a plate bending zone 1100 also may be provided in longitudinal section 1070, which may accommodate the spine to skull connection. Plate bending zones 1100 permit plate 1025 to be more securely attached with a low profile to bone portion 1020, such as a curved occipital region.

In some embodiments, housing portion 1030 may be configured to at least partially pass over anchor 1050 disposed in the pocket 1045 formed in one of the arms 1075. In other words, anchors 1050 are recessed into top surface 1035 of plate 1025 within course 1080. In addition, housing portion 1030 may be configured to lock in a position at least partially over at least one pocket 1045 formed in one of the arms 1075. As discussed above, this selective positioning allows rods 1015 to be positioned closer or further apart across a wide portion of arms 1075 without having to select the plate from ones having various sized openings. Moreover, housing portion 1030 may act to inhibit anchors 1050 from reverse threading. In some embodiments, pocket 1045 is formed within course 1080, and course 1080 may have more than one pocket 1045 formed therein. In some embodiments, course 1080 is sufficiently long relative to a length of arm 1075 to permit more than one pocket 1045 to be formed therein. In a particular embodiment, a length of course 1080 is greater than fifty percent the length of arm 1075.

At least one pocket 1045 may be configured to receive a screw locking cap as described above relative to FIGS. 1, 3 and 5. Housing portion 1030 (FIG. 9) may be configured to pass over and/or be secured above a screw locking cap, which may be disposed over anchor 1050 (FIG. 11) in pocket 1045. In addition, housing portion 1030 positioned over screw locking cap and anchor 1050 may prevent screw backout. As set screw 1145 is tightened, rod 1015 may become locked into a fixed position by pressing an engagement surface of set screw 1145 into rod 1015, pressing base 1085 of housing 1030 against top surface 1035 within channel 1080a, and pressing rod 1015 against carrier 1130 or top surface 1035 of plate 1025.

As illustrated in FIGS. 9, 10, 13, 14 and 20, the pair of arms 1075 may each form an angle θ of greater than 90° with longitudinal section 1070 of plate 1025. In other embodiments, arms 1075 may extend in a substantially orthogonal projection from longitudinal section 1070 or may include other shapes, such as a delta (or triangular) shape. In another embodiment, course 1080 may be provided in plate 1025 without distinctly formed "arms".

Referring to FIGS. 9, 10, 14, and 20, course 1080 formed within sidewalls 1026 may be formed with an inwardly projecting top shelf 1110. A channel 1080a may be provided between top shelf 1110 and another portion of course 1080 for receipt of base 1085 of housing portion 1030. In an embodiment, course 1080 may run along substantially all of the length of arm 1075. In another embodiment, course 1080 may run along only a portion of the length of arm 1075. In addition, course 1080 may be configured to extend into longitudinal section 1070 or may be configured to remain within a central portion of the length of arm 1075.

Figure 12:
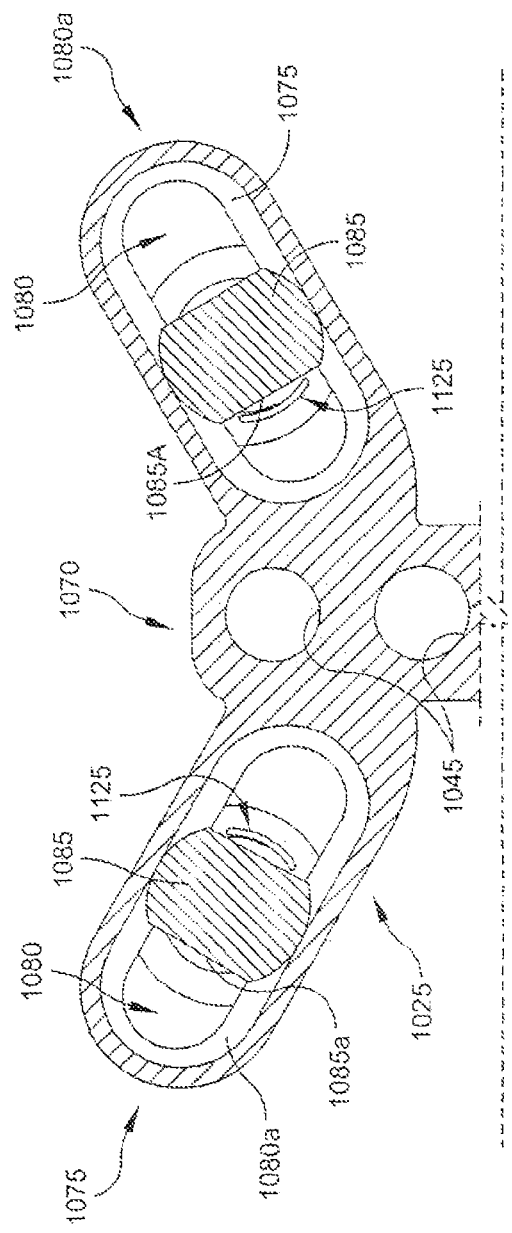
FIG. 12 is a cross-sectional view of housing portions in attachment with the plate.
Figure 13:
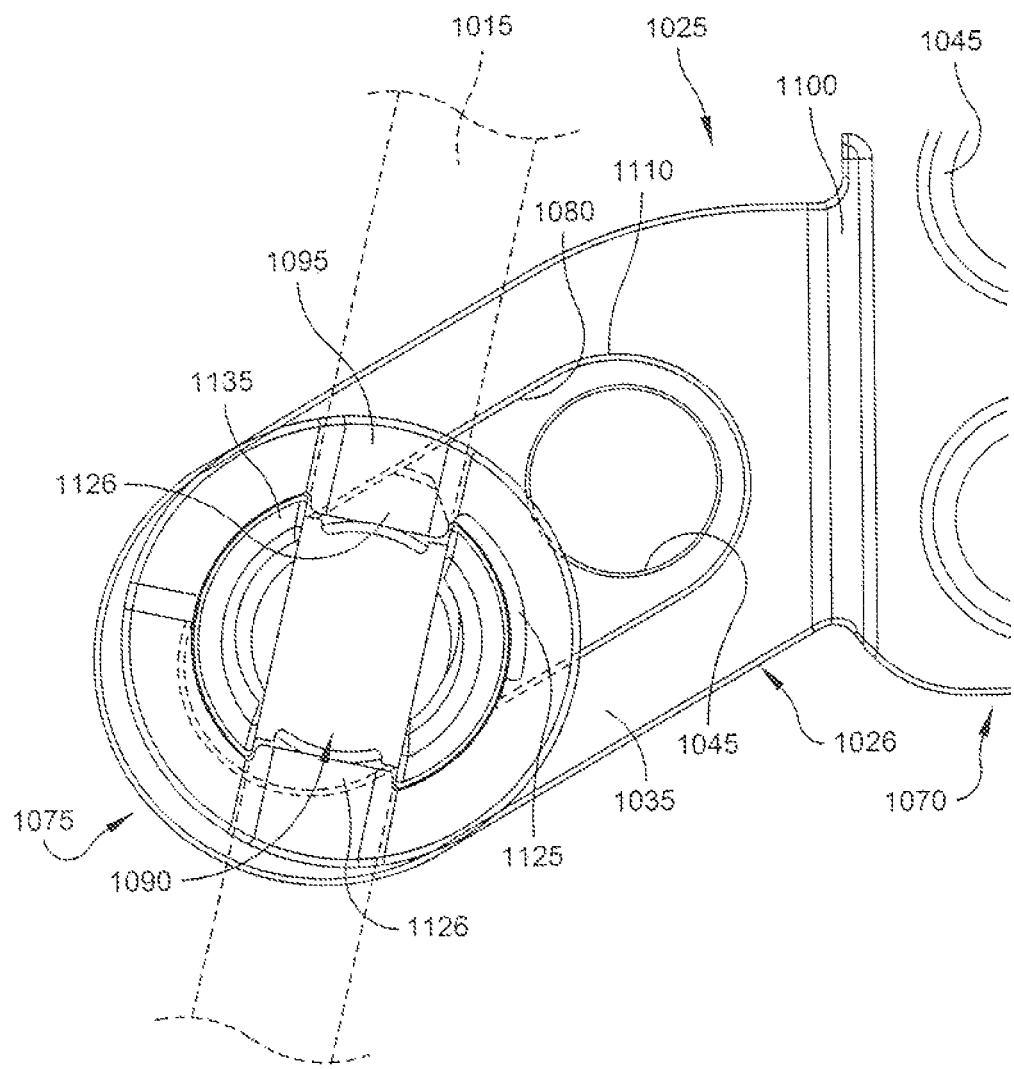
FIG. 13 illustrates a view of the arm portion of the occipital plat of FIG. 9; of an occipital plate having adjustable rod connectors mounted on opposing lateral arms.
Figure 14:
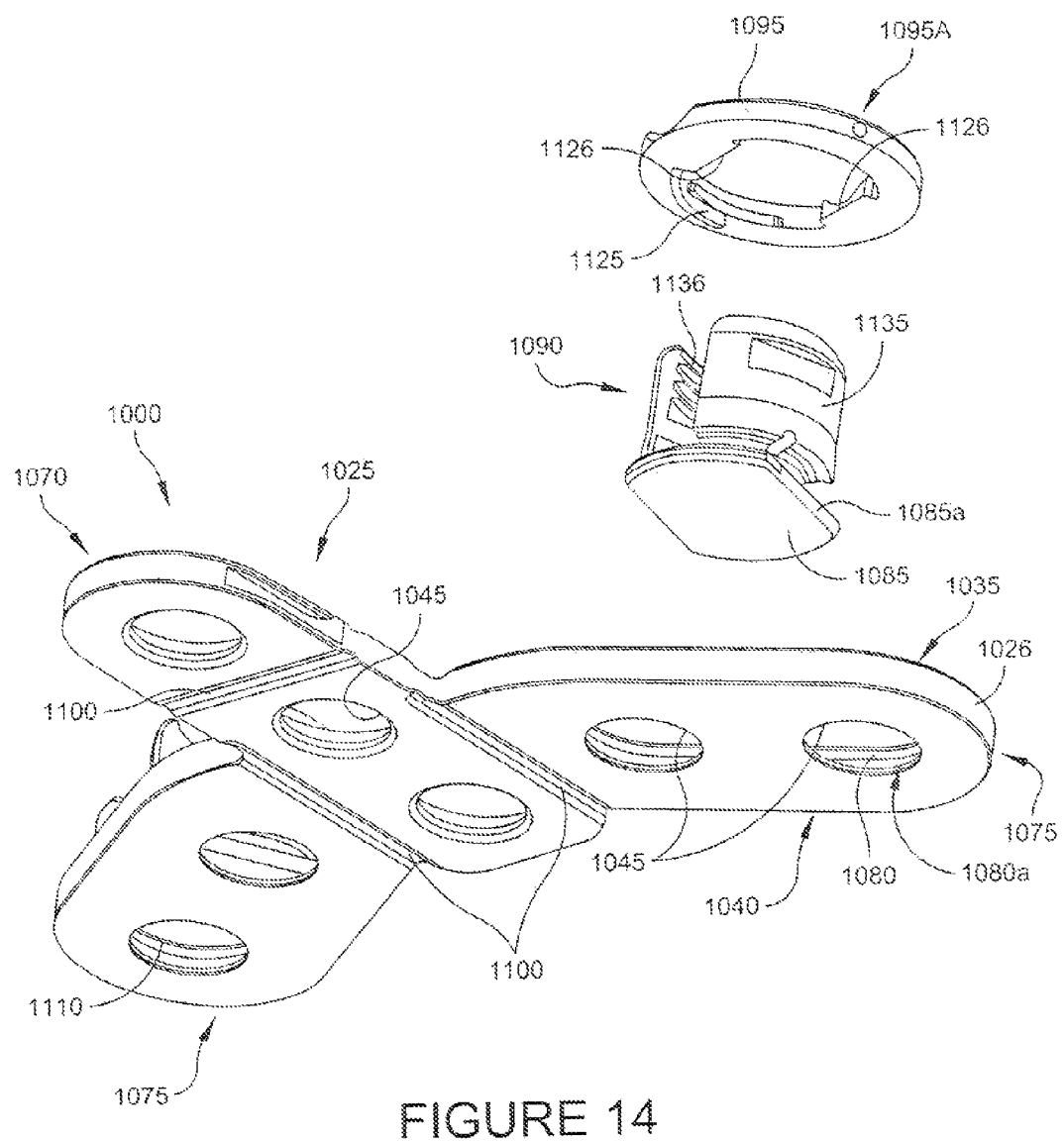
FIG. 14 illustrates a partially exploded schematic view of the occipital plate with a housing and attachment ring portion for adjustably fixing a rod to the plate.
Figure 15:
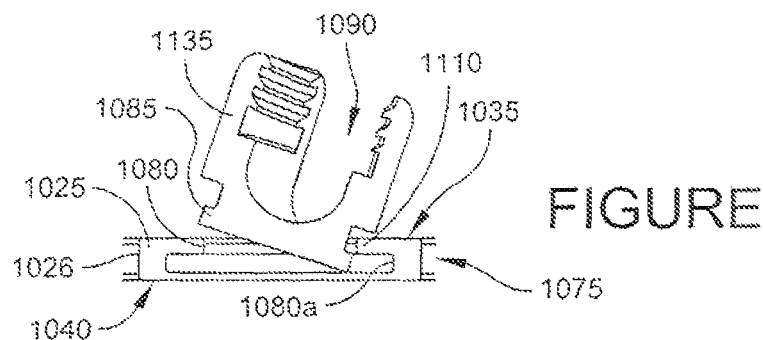
FIGS. 15-19 illustrate insertion of the base of housing into an opening in the plate.
Figure 16:
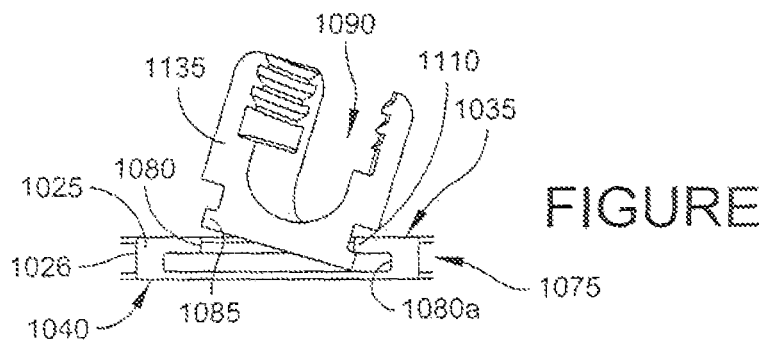
Figure 17:
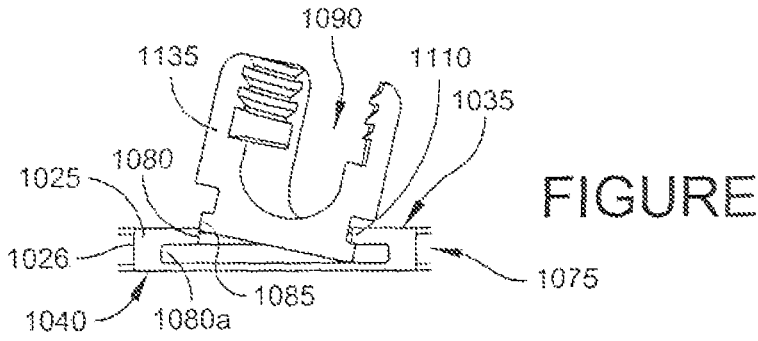
Figure 18:
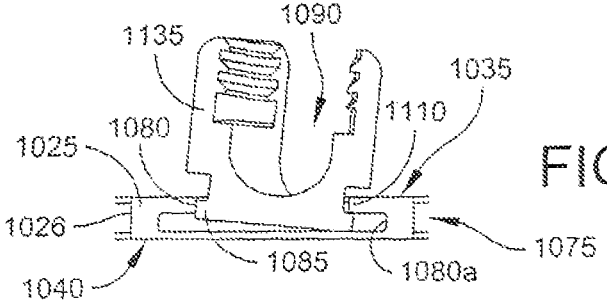
Figure 19:
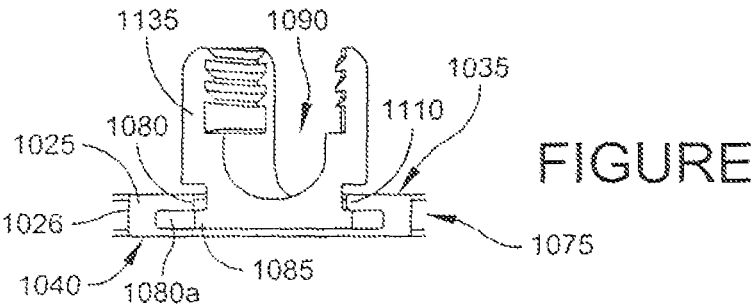
Figure 20:
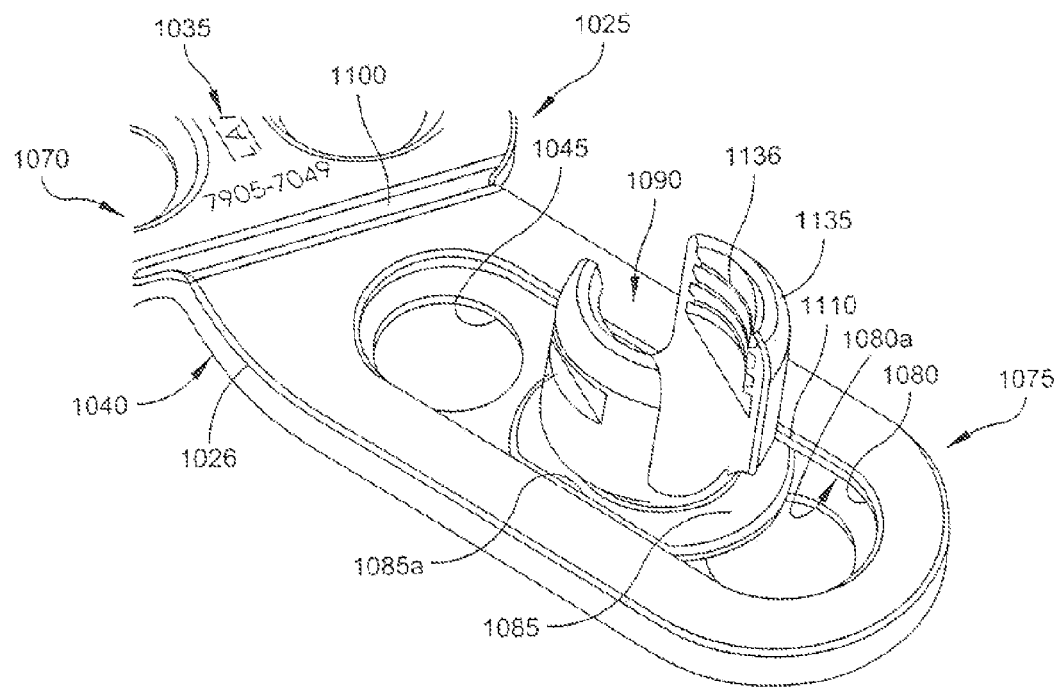
FIG. 20 illustrates a perspective view of the housing within one arm of the plate.

Looking at FIGS. 12, 13, and 14, in some embodiments a rotational limit stop 1125 extends downwardly from the bottom surface of the attachment ring 1095 in the shape of an arcuate tab. Indexing tabs 1126 project inwardly from opposite sides of the attachment ring 1095 into the central aperture of the attachment ring 1095. Referring to FIGS. 15-19, base 1085 has a width across the flats 1085a wider than the course 1080 such that the base extends into the channel 1080a. In order to insert the base 1085 into the channel, the base is tilted at an angle relative to the arm 1075 and one flat is inserted into channel 1080a under the shelf 1110. The opposite flat is then lowered into the course 1080 until it rests in the position shown in FIGS. 19 and 20. The housing portion 1030 is then rotated until the length of the base engages the channel 1080a as shown in FIGS. 9-13 and best seen in FIG. 12. In some embodiments, the length of base 1085 is approximately the same as the width of channel 1080a. In some embodiments, base 1085 is disposed between the upper and lower surfaces of plate 1025 when base 1085 is positioned in channel 1080a. Attachment ring 1095 is then pressed over the housing portion 1030 with the indexing tabs 1126 engaged with the passageway 1090 until the rotation limit stop 1125 engages the course 1080. The rotation limit stop abuts the sides of the course 1080 to allow only limited rotation of the attachment ring 1095 relative to the course 1080. The indexing tabs 1126 prevent relative rotation between the housing portion 1030 and the attachment ring. Therefore, the rotation limit stop 1125 limits rotation of the housing portion and prevents the flats 1085a from re-aligning with the course 1080. Thus the housing portion 1030 cannot be inadvertently disassembled from the arm 1075 as long as the attachment ring 1095 is in place. The arcuate length of the rotation limit stop 1125 may be varied to permit different ranges of rotation of the housing portion 1030. As seen in FIG. 13, the rotation limit stop 1125 is abutting the course 1080 preventing further clockwise rotation of the housing portion 1030. The housing may be rotated counter clockwise until the rotation limit stop 1125 abuts the opposite side of the course 1080. The range of rotation may be for example between about five (5) degrees and about sixty (60) degrees; more particularly between about 15 and 30 degrees; more particularly between about 20 and 25 degrees. In one embodiment, full rotation is 30 degrees, or 15 degrees in each direction from housing vertical position. The selected range not only prevents disassembly of the housing portion 1030 from the arm 1075, but also provides a convenient range of adjustability for rod 1015.

Housing portion 1030 may be attached to plate 1025 during surgery before or after it is attached to bone portion 1020, or it may be attached prior to surgery. If attached prior to surgery it may be attached such that it is not able to be easily disassembled by the user.

Attachment ring 1095 may be sized to snap fit, or attach with hardware through hole 1095A (FIGS. 9 AND 14). Having saddle 1135 rotatably coupled to course 1080 allows for selective orientation of rod 1015 and housing portion 1030. Housing portion 1030 may include a set screw 1145 sized for engagement with saddle 1135 such as by a threaded engagement between internal threads 1136 in saddle 1135 and corresponding external threads 1146 on set screw 1145 as shown. However, any compression fitting as is generally known in the art is useable. Set screw 1145 and saddle 1135 may be configured to selectively retain rod 1015 when set screw 1145 is tightened a predetermined amount into saddle 1135. The selective rotation of saddle 1135 with respect to arm 1075 allows rods 1015 to be positioned in various orientations without having to select from various sized attachment apparatus to provide alternative orientations.

In one embodiment, base 1085, ring 1095, saddle 1135, and set screw 1145 may be sized to lock rotation of rod 1015 and lock translation of saddle 1135 with respect to course 1080 when set screw 1145 is tightened a predetermined amount onto rod 1015 as discussed relative to the embodiment of FIGS. 7-8. In one embodiment, base 1085, ring 1095, saddle 1135, and set screw 1145 may be sized to lock rotation of rod 1015 chosen from a range of diameters. The range of diameters may include rods of about 3.0 mm to about 4.5 mm. In another embodiment, the range of rod diameters includes diameters from about 3.5 mm to about 4.0 mm.

In an embodiment (not shown), an add-on expansion may be provided for one or both of the arm portions 1075. A connector of the expansion add-on may be configured to attach to the course 1080.

Figure 21:
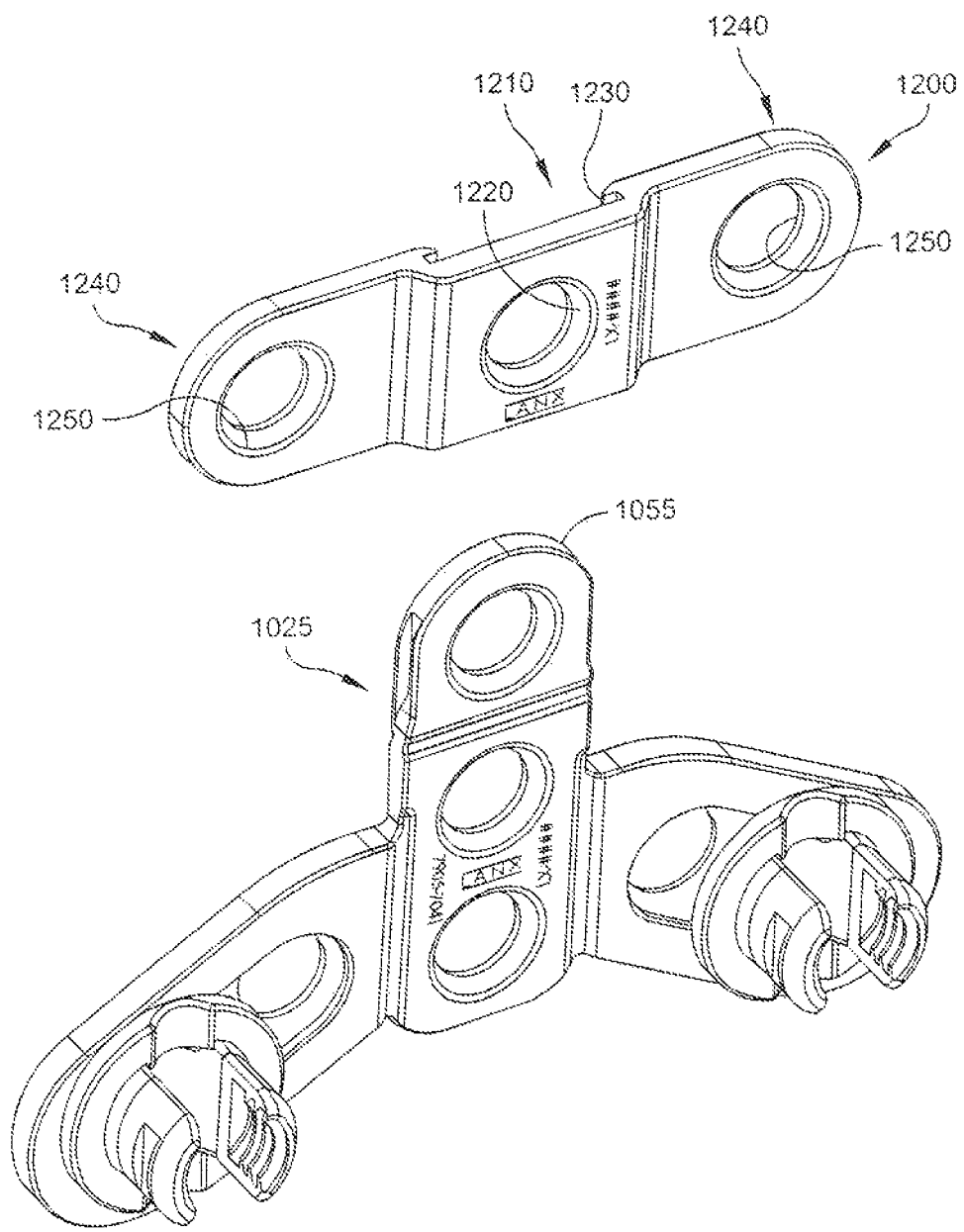
FIGS. 21 and 22 illustrate an extension member in use with the occipital plate of FIG. 9.
Figure 22:
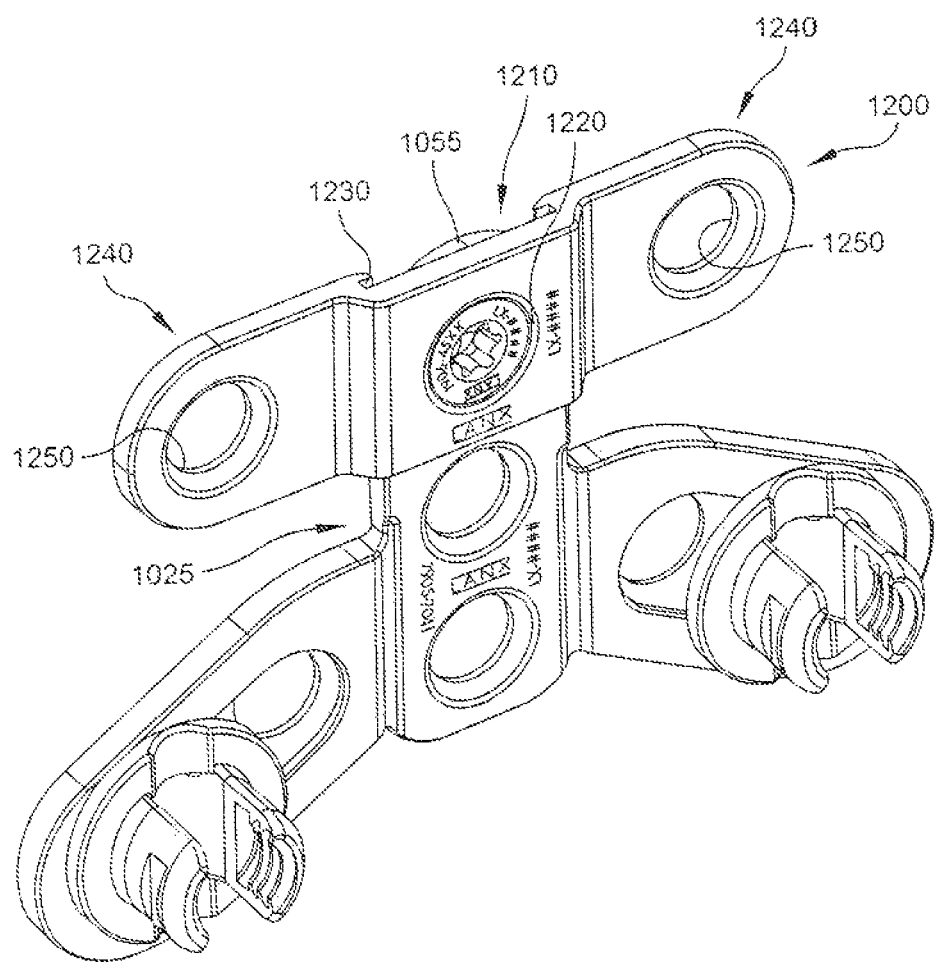

In another embodiment as shown in FIGS. 21 and 22, an add-on expansion or extension member 1200 is coupled to one or both ends of the central elongate portion of plate 1025. For example, add-on extension member 1200 may be coupled to first end 1055. Extension member 1200 has a central portion 1210 having an anchor opening 1220. Central portion 1210 further includes, in some embodiments, a lip portion 1230 to engage a corresponding slot on the edge of first end 1055. In this manner, central portion 1210, and more specifically anchor opening 1220, may be aligned with a pocket in first end 1055. It will be appreciated that plate 1025 and extension member 1200 may be coupled using other methods or devices, including by pins, posts, clips, adhesives, or tongue and groove, dovetails, or other physical arrangements.

As best seen in FIG. 22, in some embodiments a single anchor may be disposed through the aligned anchor opening 1220 and the pocket in first end 1055 for coupling plate 1025 and extension member 1200 to a bone portion, such as an occipital bone. Extension member 1200 further may include one or more wings 1240 which extend out from central portion 1210. Wings 1240 each may include one or more anchor openings 1250 for receipt of an anchor, a bone screw, or the like. In a particular embodiment, wings 1240 are generally orthogonal to the central elongate portion of plate 1025.

What is claimed is:

1. An orthopedic fixation system for attachment of a rod to a bone portion, the orthopedic fixation system comprising:
    a plate having an upper surface and a lower surface in opposition to one another, at least one pocket formed through the upper and lower surfaces, the pocket configured to receive an anchor for coupling the plate to the bone portion, a first end and a second end in opposition to one another, a line extending between the first end and the second end defining a longitudinal section of the plate, at least one arm portion extending at an angle from the longitudinal section of the plate, the at least one arm portion having a course formed by an inwardly projecting top shelf providing a channel; and
    a housing having a base configured for slideable engagement within the course to allow selective positioning of the housing along the arm portion, the housing defining a passageway configured for slideable engagement with the rod to allow selective positioning of the rod and the housing with respect to one another, a rotational stop at least partially disposed in the course which limits the amount of rotation of the housing relative to the arm portion, and a compression fitting configured for engagement with the housing and the rod so as to allow selective fixation of the housing along the arm portion and the rod and the housing with respect to one another,
    wherein the course comprises an opening in the upper surface of the arm portion, the opening having a width, wherein the base has a length and a width, and wherein both the base length and the base width are larger than the opening width.

2. The system in accordance with claim 1, further comprising a plate bending zone between the longitudinal section and the arm portion.

3. The system in accordance with claim 1, wherein the at least one pocket is formed in the longitudinal section.

4. The system in accordance with claim 1, wherein the at least one pocket is formed in the arm portion.

5. The system in accordance with claim 1, wherein the at least one pocket is formed in the course.

6. The system in accordance with claim 5, wherein the housing is adapted to slide at least partially over the anchor disposed in the pocket.

7. The system in accordance with claim 1, wherein the at least one pocket and a second pocket are formed in the course.

8. The system in accordance with claim 1, wherein the course has a length that is greater than half as long as a length of the arm portion.

9. The system in accordance with claim 1, wherein the at least one pocket is configured to receive a locking cap so as to prevent anchor back out.

10. The system in accordance with claim 1, wherein the at least one pocket forms a curved inner surface that is adapted to engage a corresponding curved outer surface of the anchor to allow angulation of the anchor with respect to the lower surface of the plate.

11. The system in accordance with claim 1, wherein the arm portion is transverse to the longitudinal section of the plate.

12. The system in accordance with claim 1, wherein the arm portion forms an angle of greater than 90° with the longitudinal section of the plate.

13. The system in accordance with claim 1, wherein the base is positioned between the plate upper surface and lower surface when the base is disposed in the channel.

14. The system in accordance with claim 1, wherein the base width is smaller than a width of the channel.

15. The system in accordance with claim 14, wherein the base length is about equal to the channel width.

16. The system in accordance with claim 1, wherein the rotational stop is coupled to the housing base.

17. The system in accordance with claim 1, wherein the rotational stop forms a protrusion that extends into the course to allow the housing to travel longitudinally in sliding relation to the arm portion while remaining along the upper surface of the plate.

18. The system in accordance with claim 1, wherein the housing includes a saddle portion for receiving the rod therein, and wherein the rotational stop limits the rotation of the saddle portion to a range of sixty degrees or less.

19. The system in accordance with claim 18, wherein the base, the ring member, and the saddle are formed to allow constrained rotation of the saddle with respect to the course.

20. The system in accordance with claim 1, wherein the housing and the plate are configured to allow attachment of the housing to the plate after the plate has been attached to the bone portion.

21. The system in accordance with claim 1, wherein the bone portion is an occipital bone.

22. An orthopedic fixation system for attachment of a rod to a bone portion, the orthopedic fixation system comprising:
   a plate having an upper surface and a lower surface in opposition to one another, at least one pocket formed through the upper and lower surfaces, the pocket configured to receive an anchor for coupling the plate to the bone portion, a first end and a second end in opposition to one another, a line extending between the first end and the second end defining a longitudinal section of the plate, at least one arm portion extending at an angle from the longitudinal section of the plate, the at least one arm portion having a course;
   a housing having a base configured for slideable engagement with the course to allow selective positioning of the housing along the arm portion, the housing defining a passageway configured for slideable engagement with the rod to allow selective positioning of the rod and the housing with respect to one another, a rotational stop at least partially disposed in the course which limits the amount of rotation of the housing relative to the arm portion, and a compression fitting configured for engagement with the housing and the rod so as to allow selective fixation of the housing along the arm portion and the rod and the housing with respect to one another; and
   a ring member having an inner surface for engagement with the housing and a lower surface for engagement with the plate.

23. The system in accordance with claim 22, wherein the ring member further comprises the rotational stop.

24. The system in accordance with claim 23, wherein the rotational stop comprises an arcuate member sized to permit a desired range of rotational movement within the course.

25. The system in accordance with claim 22, wherein the housing includes a set screw sized for engagement with a saddle forming the passageway, and
   wherein the base, the ring member, the saddle, and the set screw are sized to lock the rod therein and lock translation of the saddle with respect to the course when the set screw is tightened onto the rod.

26. The system in accordance with claim 25, wherein the base, the ring member, the saddle, and set screw are sized to lock the rod chosen from a range of rod diameters.

27. The system in accordance with claim 26, wherein the rod chosen from the range of rod diameters is 4.0 mm.

28. An occipital plate system adapted to attach a rod to an occipital bone, the occipital plate system comprising:
   a plate having spaced apart upper and lower surfaces, the plate having an elongate section defining a longitudinal axis, and first and second arms extending from the elongate section at an angle relative to the axis, the first arm having a sidewall extending between the upper and lower surfaces defining at least one course;
   a housing having a base portion, an attachment ring, and a saddle portion, the saddle portion being coupled to the attachment ring so as to permit limited rotation within the course;
   at least one rotational limit stop in connection with one of the attachment ring and the housing base so as to allow the housing to slideably engage the course for selective position thereof along the arm and to provide limited rotation of the saddle portion relative to the longitudinal axis; and
   a compression fitting adapted to engage the saddle to selectively lock a rod in the saddle and the housing to the arm portion.

29. The occipital plate system in accordance with claim 28, wherein the angle is selected from the group of angles consisting of: an obtuse angle, a right angle, or an acute angle.

30. The occipital plate system in accordance with claim 28 wherein the course comprises an inwardly projecting top shelf, providing a channel for receipt of the base of the housing portion.

* * * * *

UNITED STATES PATENT AND TRADEMARK OFFICE
CERTIFICATE OF CORRECTION

PATENT NO.        : 8,506,567 B2
APPLICATION NO.   : 12/635559
DATED             : August 13, 2013
INVENTOR(S)       : Terry Ziemek et al.

Page 1 of 1

It is certified that error appears in the above-identified patent and that said Letters Patent is hereby corrected as shown below:

In the Specification

In column 3, line 27, delete "6" and insert -- θ --, therefor.

In column 5, line 55, delete "be," and insert -- be --, therefor.

Signed and Sealed this
Fourth Day of March, 2014

Michelle K. Lee
*Deputy Director of the United States Patent and Trademark Office*